United States Patent
Oda

(10) Patent No.: US 7,640,798 B2
(45) Date of Patent: Jan. 5, 2010

(54) SEMICONDUCTOR DEVICE FOR DETECTING FLOW RATE OF FLUID

(75) Inventor: Teruo Oda, Gamagori (JP)

(73) Assignee: DENSO CORPORATION, Kariya (JP)

( * ) Notice: Subject to any disclaimer, the term of this patent is extended or adjusted under 35 U.S.C. 154(b) by 19 days.

(21) Appl. No.: 12/000,462

(22) Filed: Dec. 13, 2007

(65) Prior Publication Data

US 2008/0148842 A1 Jun. 26, 2008

(30) Foreign Application Priority Data

Dec. 22, 2006 (JP) .............................. 2006-346565

(51) Int. Cl.
*G01F 1/68* (2006.01)
(52) U.S. Cl. ................................. 73/204.26
(58) Field of Classification Search ............. 73/204.26, 73/29.01, 31.36, 335.05; 422/82.02; 338/34
See application file for complete search history.

(56) References Cited

U.S. PATENT DOCUMENTS

| | | | | |
|---|---|---|---|---|
| 4,893,508 | A * | 1/1990 | Friedman | 73/335.02 |
| 6,490,915 | B2 | 12/2002 | Yamada et al. | |
| 6,812,821 | B2 * | 11/2004 | Fujita et al. | 338/34 |
| 6,883,371 | B2 * | 4/2005 | Sugaya et al. | 73/335.05 |
| 6,983,653 | B2 | 1/2006 | Iwaki et al. | |
| 7,219,543 | B2 | 5/2007 | Tanaka et al. | |
| 7,219,544 | B2 | 5/2007 | Tanaka et al. | |
| 7,531,136 | B2 * | 5/2009 | Besnard et al. | 422/82.02 |
| 2004/0254306 | A1 | 12/2004 | Isogai et al. | |

FOREIGN PATENT DOCUMENTS

| | | |
|---|---|---|
| JP | A-10-197305 | 7/1998 |
| JP | A-2003-232765 | 8/2003 |
| JP | A-2005-257474 | 9/2005 |
| JP | A-2005-257590 | 9/2005 |
| JP | A-2006-71647 | 3/2006 |
| JP | A-2006-352666 | 12/2006 |
| JP | A-2007-155556 | 6/2007 |

\* cited by examiner

*Primary Examiner*—Jewel Thompson
(74) *Attorney, Agent, or Firm*—Posz Law Group, PLC

(57) ABSTRACT

A semiconductor device includes: a semiconductor substrate; a flow sensor having a first heater for detecting a flow rate of fluid; and a humidity sensor for detecting a humidity of the fluid. The flow sensor and the humidity sensor are disposed on the semiconductor substrate. The flow sensor is disposed around the humidity sensor. The humidity sensor is disposed on an upstream side of the first heater. Since the device includes the humidity sensor, moisture in the fluid is compensated so that detection accuracy of the flow rate is improved.

14 Claims, 5 Drawing Sheets

SEMICONDUCTOR DEVICE FOR DETECTING FLOW RATE OF FLUID

CROSS REFERENCE TO RELATED APPLICATION

This application is based on Japanese Patent Application No. 2006-346565 filed on Dec. 22, 2006, the disclosure of which is incorporated herein by reference.

FIELD OF THE INVENTION

The present invention relates to a semiconductor device for detecting a flow rate of fluid.

BACKGROUND OF THE INVENTION

A semiconductor device for detecting a flow rate of fluid is known as disclosed in, for example, Japanese Patent No. 3,468,731 corresponding to U.S. Pat. No. 6,490,915.

In a semiconductor of this kind, a heating element (heating resistance element) and a temperature sensing element (temperature sensing resistance element) for sensing temperature of a portion around the heating element are formed on a semiconductor substrate, and a flow detector for detecting flow rate of a fluid is constructed.

Fluid (for example, air) contains moisture. When the flow rate of the fluid is detected by the semiconductor device, therefore, an error occurs only by the amount of the moisture content. Such an error is not preferred in uses requiring high-precision flow rate (air volume), particularly, like in fuel injection control of an internal combustion engine of a vehicle.

SUMMARY OF THE INVENTION

In view of the above-described problem, it is an object of the present disclosure to provide a semiconductor device for detecting a flow rate of fluid.

According to a first aspect of the present disclosure, a semiconductor device includes: a semiconductor substrate; a flow sensor having a first heater for detecting a flow rate of fluid; and a humidity sensor for detecting a humidity of the fluid. The flow sensor and the humidity sensor are disposed on the semiconductor substrate. The flow sensor is disposed around the humidity sensor. The humidity sensor is disposed on an upstream side of the first heater.

Since the above device includes the humidity sensor, moisture in the fluid is compensated so that detection accuracy of the flow rate is improved. Further, the humidity sensor is disposed near the flow sensor, the humidity near the flow sensor is detected by the humidity sensor so that the detection accuracy of the flow rate is much improved. Furthermore, since the humidity sensor and the flow sensor are disposed on the same substrate, the dimensions of the device are minimized. Further, the humidity sensor is not substantially affected by heat generated by a heater in the flow sensor humidity sensor. Thus, the detection accuracy of the flow rate is improved.

According to a second aspect of the present disclosure, a semiconductor device includes: a semiconductor substrate; a flow sensor for detecting a flow rate of fluid; a humidity sensor for detecting a humidity of the fluid; a resin mold for molding a part of the semiconductor substrate; and a lead terminal, a part of which is molded in the resin mold. The flow sensor and the humidity sensor are disposed on another part of the semiconductor substrate so that the flow sensor and the humidity sensor are not covered with the resin mold. The humidity sensor is disposed on an upstream side of the first heater. The semiconductor substrate includes a concavity and a pad. The concavity is disposed opposite to the humidity sensor and the flow sensor. The pad is disposed on the substrate. The humidity sensor and the flow sensor are coupled with the pad so that the humidity sensor and the flow sensor output detection signals through the pad. The pad is coupled with the lead terminal with a wire. The resin mold molds a connection portion between the pad and the wire and the wire.

Since the above device includes the humidity sensor, moisture in the fluid is compensated so that detection accuracy of the flow rate is improved. Further, the humidity sensor is disposed near the flow sensor, the humidity near the flow sensor is detected by the humidity sensor so that the detection accuracy of the flow rate is much improved. Furthermore, since the humidity sensor and the flow sensor are disposed on the same substrate, the dimensions of the device are minimized. Further, the humidity sensor is not substantially affected by heat generated by a heater in the flow sensor humidity sensor. Thus, the detection accuracy of the flow rate is improved.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS

First Embodiment

Figure 1:
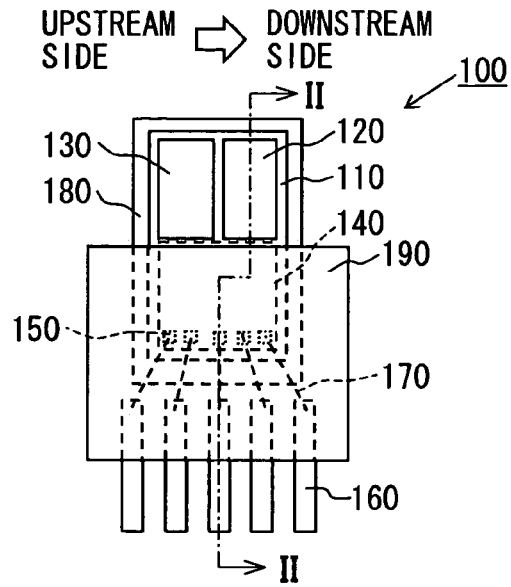
FIG. 1 is a plan view showing a schematic configuration of a semiconductor device of a first embodiment.
Figure 2:
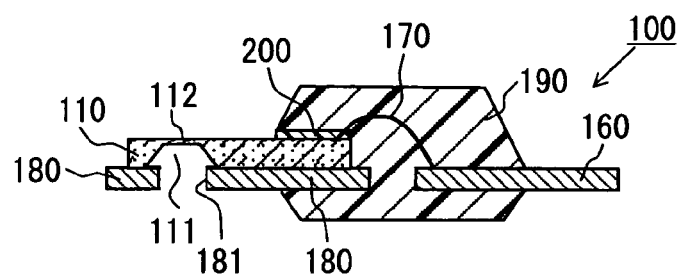
FIG. 2 is a schematic cross section taken along line II-II of FIG. 1.
Figure 3:
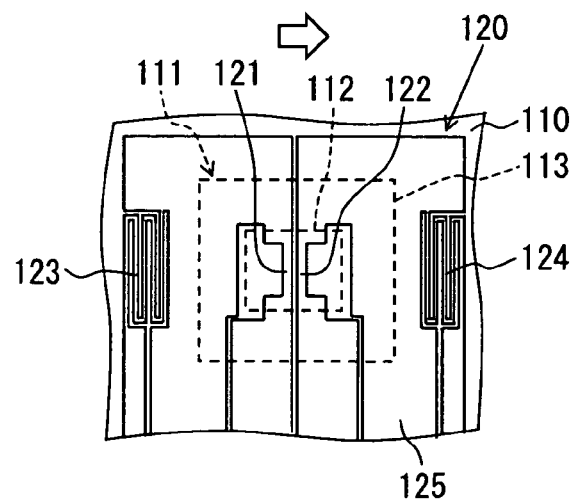
FIG. 3 is an enlarged plan view of a portion around a flow sensor.
Figure 4:
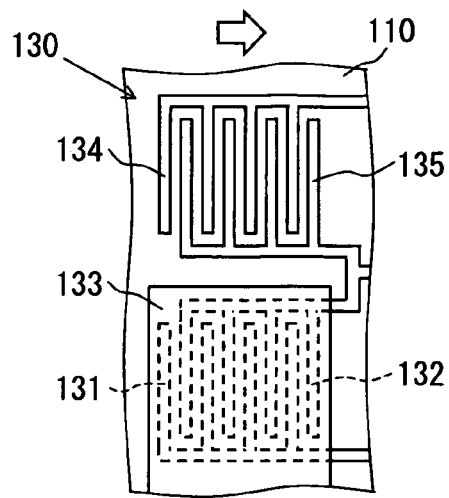
FIG. 4 is an enlarged plan view of a portion around a humidity sensor.
Figure 5:
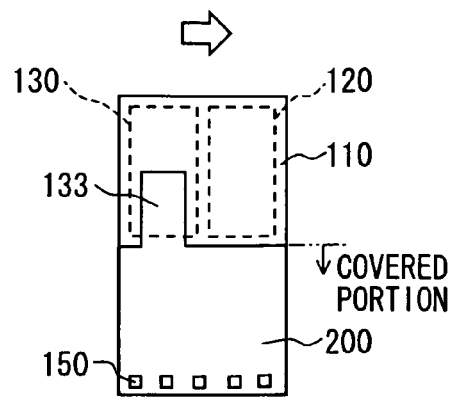
FIG. 5 is a schematic plan view showing the positional relation between a moisture sensitive film and a high polymer film over a semiconductor substrate.

FIG. 1 is a plan view showing a schematic configuration of a semiconductor device of a first embodiment of the present disclosure. FIG. 2 is a schematic cross section taken along line II-II of FIG. 1. FIG. 3 is an enlarged plan view of a portion around a flow sensor. FIG. 4 is an enlarged plan view of a portion around a humidity sensor. FIG. 5 is a schematic plan view showing the positional relation between a moisture sensitive film and a high polymer film over a semiconductor substrate. In FIG. 2, for convenience, a flow sensor and a circuit part are not shown. In FIGS. 3 and 4, for convenience, insulating films such as a protection film are not shown. In the following diagrams, a hollow arrow expresses the flow direction of a fluid in normal times.

As shown in FIGS. 1 and 2, on a semiconductor substrate 110, a flow sensor 120 for sensing a flow rate of fluid and a humidity sensor 130 for sensing humidity of the fluid are formed as main components of a semiconductor device 100. That is, the flow sensor 120 and the humidity sensor 130 are integrated on a single chip.

The flow sensor 120 is constructed as a so-called thermal flow sensor. Concretely, as shown in FIGS. 2 and 3, a cavity 111 for flow is formed as a low heat conduction area in a part of a flow sensor formation area in the silicon substrate as the semiconductor substrate 110. A thin portion 112 (membrane) of an insulting film is formed over the cavity 111 for flow. More specifically, the semiconductor substrate 110 is subject to anisotropic etching from the back side of the flow sensor formation face, thereby obtaining the thin portion 112. In FIG. 3, smaller one of two rectangular areas surrounded by broken lines is the thin portion 112, and the larger area indicates an open face 113 of the cavity 111 for flow. The thin portion 112 is formed much thinner than the other part of the semiconductor substrate 110, so that heat capacity is suppressed, and thermal insulation from the other part is assured.

As shown in FIG. 3, heating elements 121 and 122 are formed on the thin portion 112. The heating element 121 is an upstream-side heating element disposed on the upstream side in the flow direction of the fluid. The heating element 122 is a downstream-side heating element disposed on the downstream side in the flow direction of the fluid. A pair of temperature sensing elements 123 and 124 as temperature sensing resistors are formed so as to sandwich the pair of heating elements 121 and 122 in the peripheral area of the thin portion 112, which is thicker than the thin portion 112 and on the upstream side and the downstream side of the fluid, respectively. Each of the heating elements 121 and 122 and the temperature sensing elements 123 and 124 is formed as a part of a wiring part 125. The wiring part 125 also functions as a wiring connected to a circuit part 140 which will be described later. As the material of the wiring part 125, for example, a known wiring material such as polysilicon properly doped with an impurity or a metal such as Pt can be employed.

The flow sensor 120 constructed as described above has the function of generating heat according to a current supply amount by the heating elements 121 and 122 of the embodiment and, in addition, the function of sensing the temperature of itself on the basis of a change in the resistance value of itself. On the basis of heat taken by the fluid out of the heat generated by the heating elements 121 and 122 on the upstream side and the downstream side, the flow rate of the fluid is detected. On the basis of the variation in the amount of heat taken by the fluid out of the heat generated by the heating element 121 on the upstream side and the heating element 122 on the downstream side, the distribution direction of the fluid is detected. Further, on the basis of the temperature difference between the heating element 121 on the upstream side and the temperature sensing element 123 on the upstream side, and the temperature difference between the heating element 122 on the downstream side and the temperature sensing element 124 on the downstream side, the amounts of current supplied to the heating elements 121 and 122 are controlled. With respect to the details of the flow sensor 120, for example, refer to JP-A-2004-205498 corresponding to U.S. Pat. No. 6,983,653.

The humidity sensor 130 is constructed as a so-called capacitance-type humidity sensor. Concretely, as shown in FIG. 4, on the same face as the flow sensor formation face, of the silicon substrate as the semiconductor substrate 110, a pair of detection electrodes 131 and 132 are formed so as to face each other while being apart from each other via an insulating film (not shown) such as a silicon oxide film or a silicon nitride film. More specifically, the detection electrodes 131 and 132 have a comb shape. Adjacent to the detection electrodes 131 and 132, a pair of reference electrodes 134 and 135 is formed so as to face each other while being apart from each other on the same face as the detection electrode formation face. In the embodiment, the reference electrodes 134 and 135 are formed in the same pattern and made of the same material as that of the detection electrodes 131 and 132. More specifically, the detection electrodes 131 and 132 and the reference electrodes 134 and 135 are formed in the comb shape. As the material of the detection electrodes 131 and 132 and the reference electrodes 134 and 135, a known wiring material such as polysilicon properly doped with an impurity or a metal such as Pt, Al, Cu, or Au can be employed.

A protection film (not shown) such as a silicon nitride film is formed over the semiconductor substrate 110 so as to cover the detection electrodes 131 and 132 and the reference electrodes 134 and 135. On the protection film, a moisture sensitive film 133 made of a humidity sensitive material such as polyimide is formed so as to cover the detection electrodes 131 and 132 and the gaps between the detection electrodes 131 and 132. When the detection electrodes 131 and 132 and the reference electrodes 134 and 135 have corrosion resistance against moisture, it is unnecessary to form the protection film.

In the humidity sensor 130 constructed as described above, when moisture penetrates the moisture sensitive film 133, since the relative permittivity of moisture is high, the relative permittivity of the moisture sensitive film 133 changes according to the amount of penetrated moisture. As a result, the electrostatic capacity of a capacitor constructed by the detection electrodes 131 and 132 using the moisture sensitive film 133 as a part of the dielectric changes. On the other hand, the moisture sensitive film 133 is not provided on the reference electrodes 134 and 135 side. Consequently, the electrostatic capacity of a capacitor constructed by the reference electrodes 134 and 135 does not change or slightly changes. Since the amount of moisture contained in the moisture sensitive film 133 corresponds to the humidity around the humidity sensor 130, humidity can be detected from the difference between the electrostatic capacity between the detection electrodes 131 and 132 and the electrostatic capacity between the reference electrodes 134 and 135.

Over the semiconductor substrate 110, as shown in FIG. 1, other than the flow sensor 120 and the humidity sensor 130, the circuit part 140 is also formed. The circuit part 140 is constructed by devices such as a MOS transistor and a diode and wires, and is electrically connected to the flow sensor 120 and the humidity sensor 130. The circuit part 140 includes a signal processing circuit for processing signals output from the flow sensor 120 and the humidity sensor 130 and circuits for generating signals applied to the flow sensor 120 and the humidity sensor 130 at the time of detection. In FIG. 1, for convenience, the circuit part 140 is shown (the broken line in FIG. 1) in an area excluding the formation area of the flow sensor 120 and the humidity sensor 130 over the semiconductor substrate 110. The formation area of the circuit part 140 may be formed except for the cavity 111 for flow.

Pads 150 as electrodes are formed at an end of the circuit part 140 constructed on the semiconductor substrate 110. The pad 150 is connected to a lead 160 as an external output terminal via a wire 170. Therefore, the circuit part 140 can electrically transmit/receive signals to/from the outside (for example, an external ECU) via the lead 160. The semiconductor substrate 110 is fixed to a supporting member 180 by, for example, adhesion using the back side of the formation face on which the flow sensor 120 and the humidity sensor 130 as a mounting face. In the embodiment, the supporting member 180 is constructed as a part of a lead frame together with the lead 160. In a portion corresponding to the cavity 111 for flow in the supporting member 180, a through hole as a communication part 181 capable of making the fluid communicated between the cavity 111 for flow and the outside is formed. A part of the semiconductor substrate 110 including the pads 150 and excluding the formation area of the flow sensor 120 and the humidity sensor 130, a part of the supporting member 180 corresponding to a part of the semiconductor substrate 110, and a part of the wire 170 and the lead 160 are integrally covered (molded) with an encapsulation resin 190 such as epoxy resin. In the above-described lead frame, an unnecessary part is removed in a state where the encapsulation resin 190 is cured so that the lead 160 and the supporting member 180 are separated from each other as shown in FIGS. 1 and 2.

As described above, the semiconductor device 100 of the embodiment has not only the flow sensor 120 but also the humidity sensor 130, so that the flow rate detection precision can be improved as compared with that in the configuration in which water content in a fluid is not corrected.

Since the humidity sensor 130 is formed near the formation area of the flow sensor 120 on the same semiconductor substrate 110, as compared with the configuration having the humidity sensor constructed on a substrate different from the substrate of the flow sensor 120, humidity of a fluid in a position closer to the flow sensor 120 can be detected. That is, the flow rate detection precision can be further improved.

Since the flow sensor 120 and the humidity sensor 130 are formed over the same semiconductor substrate 110, the structure can be downsized as compared with the configuration having the humidity sensor formed on the substrate different from that of the flow sensor 120.

The characteristic points other than the point that the flow sensor 120 and the humidity sensor 130 are formed in one chip, of the semiconductor device 100 will now be described with reference to FIGS. 1 and 5.

First, the layout of the flow sensor 120 and the humidity sensor 130 is characterized. For example, when the humidity sensor 130 is disposed on the downstream side of the flow sensor 120, it is feared that the fluid which has taken the heat of the heating elements 121 and 122 constructing the flow sensor 120 gives heat to the humidity sensor 130 positioned on the downstream side of the heating elements 121 and 122. That is, the humidity detection precision of the humidity sensor 130 may deteriorate. In particular, when the flow sensor 120 and the humidity sensor 130 are constructed on the same face side of the semiconductor substrate 110, the problem tends to occur.

In contrast, in the embodiment, as shown in FIG. 1, the flow sensor 120 and the humidity sensor 130 are formed side by side along the fluid flow direction on the same face side of the semiconductor substrate 110, and the humidity sensor 130 is provided on the upstream side of the flow sensor 120. Therefore, when the fluid flows in the normal flow direction, heat conduction via the fluid can be suppressed. As compared with the configuration in which the humidity sensor 130 is provided on the downstream side of the flow sensor 120, the influence of heat of the heating elements 121 and 122 exerted on the humidity sensor 130 can be reduced. That is, the humidity sensor 130 can detect humidity with higher precision. Thus, at the time of obtaining the flow excluding the moisture content contained in the fluid (true flow) from the detection results of the flow sensor 120 and the humidity sensor 130, the flow detection precision can be further improved. Therefore, the semiconductor device 100 is suitable for uses requiring high-precision flow rate (air volume) like in fuel injection control of an internal combustion engine of a vehicle.

Next, the moisture sensitive film 133 as the component of the humidity sensor 130 is characterized. In the configuration that at least a part of the semiconductor substrate is covered with an encapsulation resin, it is preferable to form a high polymer film of polyimide or the like on a semiconductor substrate to increase the degree of adhesion between the encapsulation resin and the semiconductor substrate. In the embodiment, the moisture sensitive film 133 made of polyimide is employed and, as shown in FIG. 5, the moisture sensitive film 133 and a high polymer film 200 made of the same material are integrally formed. Therefore, as compared with the configuration in which the moisture sensitive film 133 and the high polymer film 200 are made of different materials, the configuration and the manufacturing process can be simplified. Since the moisture sensitive film 133 is integrated with the high polymer film 200, the holding power of the moisture sensitive film 133 is increased, and peeling and the like of the moisture sensitive film 133 exposed to the fluid can be suppressed. Further, by the integration, the structure of the semiconductor device 100 can be also downsized.

In the embodiment, to eliminate dead space in the formation area of the moisture sensitive film 133 integrated with the high polymer film 200 in the portion of the semiconductor substrate 110 exposed from the encapsulation resin 190, the flow sensor 120 and the humidity sensor 130 are formed side by side along the fluid flow direction, and the detection electrodes 131 and 132 forming the humidity sensor 130 are set as a portion which is covered with the encapsulation resin 190. However, the moisture sensitive film 133 can be formed anywhere except for the thin portion 112. In the case of forming the moisture sensitive film 133 on not only the detection electrodes 131 and 132 but also the other part (for example, a part of the flow sensor 120), the formation area becomes large. Consequently, although the cost increases, manufacturing is facilitated.

In the configuration in which the moisture sensitive film 133 and the high polymer film 200 are integrally formed, there is the possibility that moisture enters the high polymer film 200 via the humidity sensitivity film 133 and the connection portion between the pad 150 and the lead 160 corrodes. In the embodiment, polyimide having a mesh structure in which terminals of a molecular chain as a base are connected to each other is employed for the moisture sensitive film 133 and the high polymer film 200. Examples of such polyimide include polyimide having a mesh structure obtained by forming a benzene ring by heating polyamide acid terminated with terminal acetylene to cause reaction between acetylene at the terminals at the time of curing, and polyamide obtained by dehydrating and ring-closing polyamide acid having a mesh structure obtained by coupling terminals of a molecular chain as a base. Refer to the details of the polyimide disclosed in JP-A-2003-232765 and 2006-71647. When such polyimide having the mesh structure is employed, swelling of the moisture sensitive film 133, which occurs when absorption water coagulates at high temperature under high humidity, can be suppressed. In other words, penetration of moisture to polyimide molecules is suppressed. The high polymer film 200 is exposed from the encapsulation resin 190 directly or indirectly via the moisture sensitive film 133, and corrosion can be suppressed also in the configuration in which the connection part between the pad 150 and the lead corrodes due to moisture.

Figure 6:
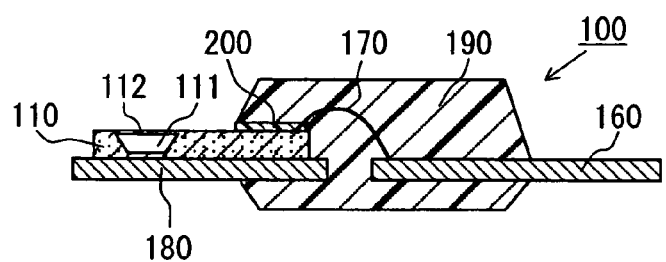
FIG. 6 is a cross section showing a modification.

In the embodiment, the semiconductor substrate 110 is subject to anisotropic etching from the back side of the flow sensor formation face, thereby forming the cavity 111 for flow. That is, the open face 113 of the cavity 111 for flow is on the back side of the flow sensor formation face of the semiconductor substrate 110. However, the configuration of the cavity 111 for flow is not limited to the example. It is sufficient to form the thin portion 112. For example, as shown in FIG. 6, the cavity 111 for flow formed by etching the semiconductor substrate 110 from the flow sensor formation face side can be also employed. In this case, since the cavity 111 for flow is open (not shown) on the flow sensor formation face side, it is unnecessary to provide the communication part 181 in the supporting member 180. FIG. 6 is a cross section showing a modification and corresponds to FIG. 2.

Figure 7:
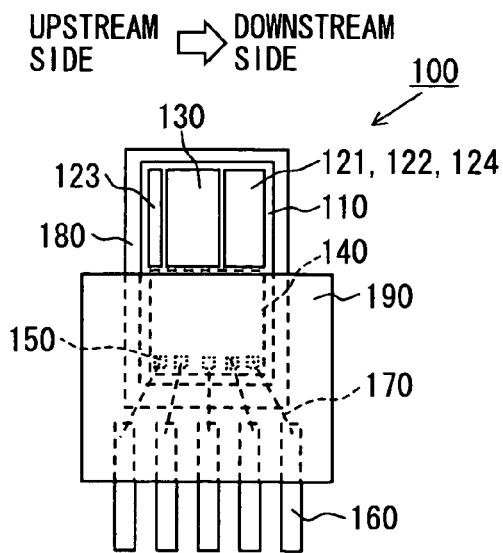
FIG. 7 is a plan view showing a second modification.

In the embodiment, the flow sensor 120 and the humidity sensor 130 are formed side by side along the fluid flow direction on the same face side of the semiconductor substrate 110, and the humidity sensor 130 is provided on the upstream side of the flow sensor 120. However, even when the arrangement direction of the flow sensor 120 and the humidity sensor 130 is not along the fluid flow direction, if the humidity sensor 130 is on the upstream side of the flow sensor 120 in the flow direction of the fluid, heat conduction via the fluid can be suppressed. The heat conduction via the fluid is mainly with heat from the heating elements 121 and 122 constructing the flow sensor 120, so that it is sufficient to provide at least the heating elements 121 and 122 on the downstream side of the humidity sensor 130. For example, as shown in FIG. 7, the heating element 123 on the upstream side in the wiring part 125 as a component of the flow sensor 120 is provided on the upstream side of the humidity sensor 130, and the remaining heating elements 121 and 122 and the temperature sensing element 124 may be provided on the downstream side. FIG. 7 is a plan view showing a modification and corresponds to FIG. 1.

Second Embodiment

Figure 8:
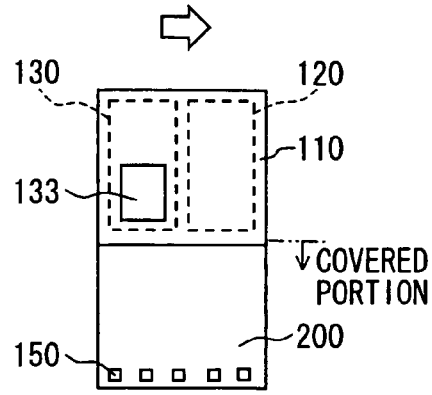
FIG. 8 is a schematic plan view showing the positional relation between a moisture sensitive film and a high polymer film over a semiconductor substrate in a semiconductor device of a second embodiment.
Figure 9:
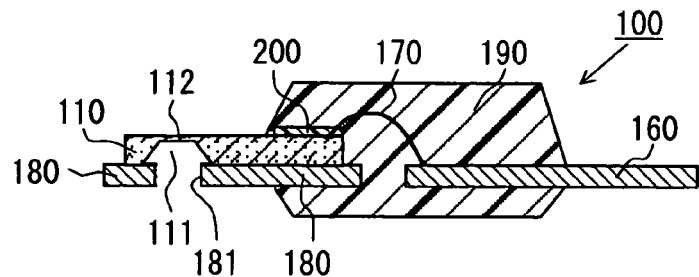
FIG. 9 is a schematic cross section of a semiconductor device.

A second embodiment of the present disclosure will be described with reference to FIGS. 8 and 9. FIG. 8 is a schematic plan view showing the positional relation between a moisture sensitive film and a high polymer film over the semiconductor substrate in a semiconductor device of the second embodiment. FIG. 9 is a schematic cross section of the semiconductor device. FIG. 9 corresponds to FIG. 2 showing the first embodiment and, for convenience like in FIG. 2, a flow sensor and a circuit part are not shown.

Since the semiconductor device of the second embodiment is largely common to that of the first embodiment, the detailed description of the common parts will not be repeated hereinbelow, and different parts will be described with concentration. The same reference numerals are designated to the same elements as those of the first embodiment.

In the first embodiment, an example of integrating the moisture sensitive film 133 and the high polymer film 200 was described. In contrast, the second embodiment is characterized by the points that the moisture sensitive film 133 and the high polymer film 200 are made of the same material such as polyimide and, as shown in FIGS. 8 and 9, the moisture sensitive film 133 and the high polymer film 200 are formed so as to be separate from each other, and the high polymer film 200 is completely covered with the encapsulation resin 190. The second embodiment has the same configuration as that of the first embodiment except for the point that the moisture sensitive film 133 and the high polymer film 200 are formed so as to be separate from each other, and the effect is similar.

In the semiconductor device 100 of the second embodiment, the high polymer film 200 is not directly exposed to the outside of the encapsulation resin 190 and is not also indirectly exposed via the moisture sensitive film 133. Consequently, even in the configuration in which the connection part between the pad 150 and the lead 160 does not corrode due to moisture, the corrosion can be suppressed.

Even in the configuration where the moisture sensitive film 133 and the high polymer film 200 are separated from each other, the moisture sensitive film 133 and the high polymer film 200 are made of the same material. As compared with the configuration in which the moisture sensitive film 133 and the high polymer film 200 are made of different materials, the configuration and the manufacturing process can be simplified.

The configuration of the humidity sensitivity film 133 and the high polymer film 200 of the second embodiment can be also applied to the configuration of the modification (FIGS. 6 and 7) of the first embodiment.

In the second embodiment, the high polymer film 200 formed separate from the moisture sensitive film 133 is completely covered with the encapsulation resin 190. However, a part of the high polymer film 200 formed separately from the moisture sensitive film 133 may be exposed to the outside from the encapsulation resin 190. In such a configuration, the high polymer film 200 is disposed to the end of the encapsulation resin 190, so that peeling of the sealing resin 190 from the semiconductor substrate 110 can be suppressed. Since the high polymer film 200 is exposed directly to the outside, as described in the first embodiment, it is preferable to employ polyimide having the mesh structure.

In the configuration where the moisture sensitive film 133 and the high polymer film 200 are formed separate from each other, the holding power of the moisture sensitive film 133 to the semiconductor substrate 110 is lower than that of the integral configuration. For example, by using a silane coupling material, deterioration in the holding power of the moisture sensitive film 133 to the semiconductor substrate 110 may be suppressed.

Third Embodiment

Figure 10:
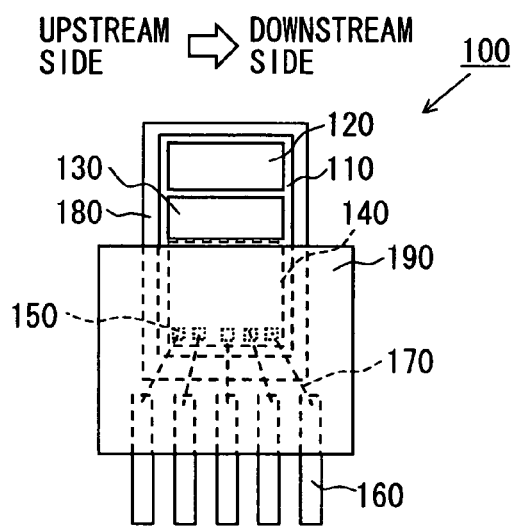
FIG. 10 is a plan view showing a schematic configuration of a semiconductor device of a third embodiment.

A third embodiment of the present disclosure will now be described with reference to FIG. 10. FIG. 10 is a plan view showing a schematic configuration of a semiconductor device of the third embodiment, and corresponds to FIG. 1 showing the first embodiment.

Since the semiconductor device of the third embodiment is largely common to that of the first embodiment, the detailed description of the common parts will not be repeated hereinbelow, and different parts will be described with concentration. The same reference numerals are designated to the same elements as those of the first embodiment.

In the first embodiment, the flow sensor 120 and the humidity sensor 130 are formed side by side along the fluid flow direction on the same side of the semiconductor substrate 110, and the humidity sensor 130 is provided on the upstream side of the flow sensor 120. On the other hand, the third embodiment is characterized by the point that, as shown in FIG. 10, the humidity sensor 130 is formed in a portion near the flow sensor 120 excluding an upstream area and a downstream area of the flow sensor 120 in the fluid flow direction. For example, in the third embodiment, the flow sensor 120 and the humidity sensor 130 are formed in parallel with the fluid flow direction. The configuration of the third embodiment is similar to that of the first embodiment except for the layout of the flow sensor 120 and the humidity sensor 130 over the semiconductor substrate 110 and the effect of the third embodiment is also similar to that of the first embodiment.

As described above, in the semiconductor device 100 of the third embodiment, the flow sensor 120 and the humidity sensor 130 are formed in parallel with the fluid flow direction, so that heat conduction from the flow sensor 120 to the humidity sensor 130 via the fluid can be suppressed. Therefore, the humidity sensor 130 can detect humidity with high precision and, moreover, the flow detection precision can be improved.

With the configuration of the third embodiment, even when the fluid flows in the direction opposite to that in normal times (the direction opposite to the open-arrow direction shown in FIG. 10), heat conduction to the humidity sensor 130 via the fluid from the flow sensor 120 can be suppressed.

The layout of the flow sensor 120 and the humidity sensor 130 shown in the third embodiment can be also applied to the modification (FIGS. 6 and 7) of the first embodiment and the configuration shown in the second embodiment.

Fourth Embodiment

Figure 11:
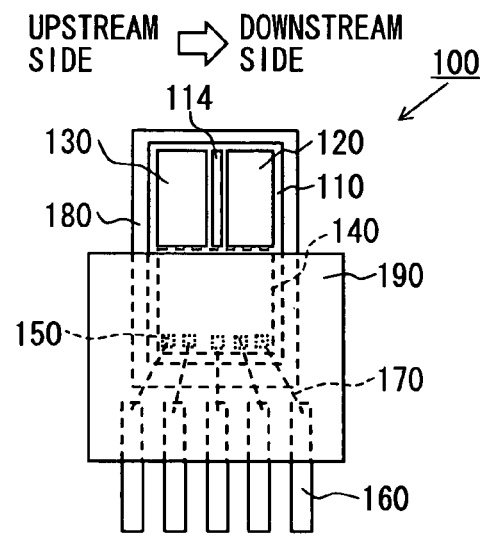
FIG. 11 is a plan view showing a schematic configuration of a semiconductor device of a fourth embodiment.
Figure 12:
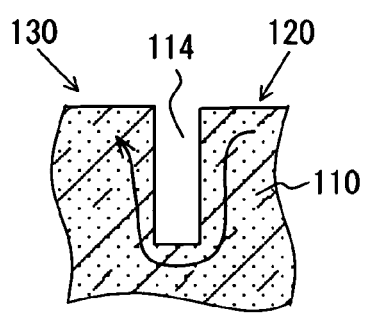
FIG. 12 is a schematic cross section showing suppression of heat conduction from a flow sensor to a humidity sensor via a semiconductor substrate.

A fourth embodiment of the present disclosure will be described with reference to FIGS. 11 and 12. FIG. 11 is a plan view showing a schematic configuration of a semiconductor device of the fourth embodiment and corresponds to FIG. 1 shown in the first embodiment. FIG. 12 is a schematic cross section showing suppression of heat conduction from the flow sensor to the humidity sensor via the semiconductor substrate. In FIG. 12, for convenience, the configurations of the flow sensor and the humidity sensor are not shown but only positions are shown.

Since the semiconductor device of the fourth embodiment is largely common to that of the first embodiment, the detailed description of the common parts will not be repeated hereinbelow, and different parts will be described with concentration. The same reference numerals are designated to the same elements as those of the first embodiment.

In the first embodiment, the flow sensor 120 and the humidity sensor 130 are formed side by side along the fluid flow direction on the same face side of the semiconductor substrate 110, and the humidity sensor 130 is provided on the upstream side of the flow sensor 120, thereby suppressing conduction of heat from the flow sensor 120 to the humidity sensor 130 via the fluid. On the other hand, the fourth embodiment is characterized by the points that conduction of heat from the flow sensor 120 to the humidity sensor 130 via the fluid is suppressed and, in addition, conduction of heat from the flow sensor 120 to the humidity sensor 130 via the semiconductor substrate 110 is suppressed.

Concretely, as shown in FIG. 11, a trench 114 as a groove having a predetermined depth from the flow sensor formation face of the semiconductor substrate 110 is formed in a portion between the formation area of the flow sensor 120 and the formation area of the humidity sensor 130 and over which the flow sensor 120 and the humidity sensor 130 face each other. The fourth embodiment has the same configuration as that of the first embodiment except for the point that the trench 114 is formed, and the effect is similar. The trench 114 can be formed by etching such as reactive ion etching (RIE).

In the semiconductor device 100 of the fourth embodiment, as shown in FIG. 12, the trench 114 is formed between the formation area of the flow sensor 120 and the formation area of the humidity sensor 130. The heat conduction path from the flow sensor 120 to the humidity sensor 130 via the semiconductor substrate 110 is longer than that in the configuration in which no trench 114 is formed. That is, heat conduction from the flow sensor 120 to the humidity sensor 130 via the semiconductor substrate 110 can be suppressed. Therefore, the humidity sensor 130 can detect humidity with high precision and, moreover, the flow rate detection precision can be improved.

In the fourth embodiment, the trench 114 is formed between the formation area of the flow sensor 120 and the formation area of the humidity sensor 130 and in a portion over which the flow sensor 120 and the humidity sensor 130 face each other. However, it is sufficient to form the trench 114 at least between the formation area of the heating elements 121 and 122 and the formation area of the humidity sensor 130 facing the formation area of the heating elements 121 and 122.

In the fourth embodiment, the trench 114 is formed in the configuration shown in the first embodiment. However, by forming the trench 114 regardless of the positional relation between the flow sensor 120 and the humidity sensor 130, heat conduction from the flow sensor 120 to the humidity sensor 130 via the semiconductor substrate 110 can be suppressed. Therefore, the trench 114 can be also applied to the modification configurations (FIGS. 6 and 7) of the first embodiment and the second embodiment.

In the fourth embodiment, the trench 114 is a cavity. However, the trench 114 may be filled with a material having thermal conductivity lower than that of the semiconductor substrate 110. Also with such a configuration, heat conduction from the flow sensor 120 to the humidity sensor 130 via the semiconductor substrate 110 can be suppressed. When the trench 114 is filled with a porous material (for example, porous silicone or porous insulating film), it is more effective to suppress heat conduction.

Fifth Embodiment

Figure 13:
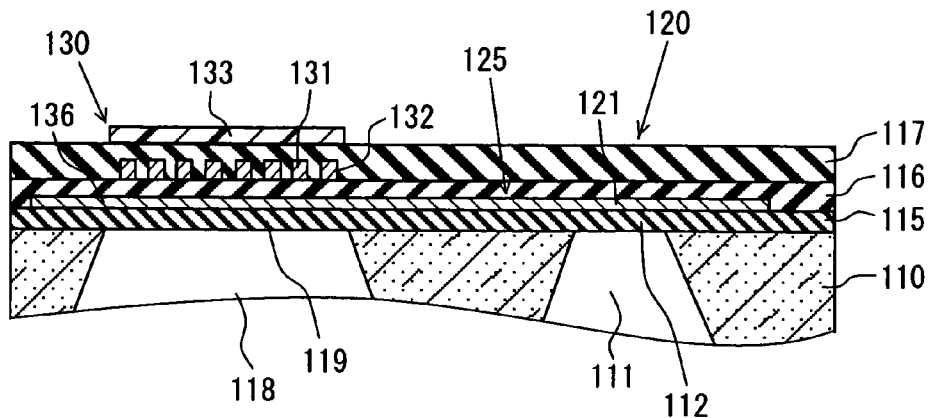
FIG. 13 is a cross section showing a schematic configuration of a semiconductor device of a fifth embodiment.
Figure 14:
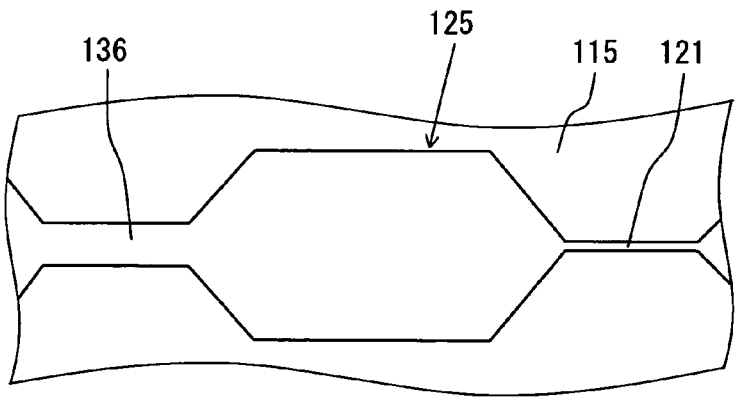
FIG. 14 is a schematic plan view showing wiring widths of a heating element and a dehumidification heater in a wiring part.

A fifth embodiment of the present disclosure will be described with reference to FIGS. 13 and 14. FIG. 13 is a cross section showing a schematic configuration of a semiconductor device of the fifth embodiment. FIG. 14 is a schematic plan view showing wiring widths of a heating element and a dehumidification heater in a wiring part.

Since the semiconductor device of the fifth embodiment is largely common to that of the first embodiment, the detailed description of the common parts will not be repeated hereinbelow, and different parts will be described with concentration. The same reference numerals are designated to the same elements as those of the first embodiment.

In the fifth embodiment, as shown in FIG. 13, a dehumidification heater 136 for heating the humidity sensor 130 by generating heat by passage of current is formed over the semiconductor substrate 110. The dehumidification heater 136 is provided to recover the moisture sensitive film 133 by evaporating the moisture which is captured in the moisture sensitive film 133 due to deterioration in the moisture sensitive film 133. The first characteristic is that the dehumidification heater 136 and the heating elements 121 and 122 constructing the flow sensor 120 (only the heating element 121 is shown in FIGS. 13 and 14) are integrally formed as the wiring part 125 made of the same material as shown in FIGS. 13 and 14. The second characteristic is that a cavity 118 for dehumidification as a low thermal conduction area is formed also in an area in the semiconductor substrate 110 corresponding to the humidity sensor 130.

Concretely, as shown in FIG. 13, the wiring part 125 including the heating elements 121 and 122 and the dehumidification heater 136 is formed over the semiconductor substrate 110 via an insulating film 115 (for example, a silicon nitride film and a silicon oxide film). Although not shown in FIG. 13, the wiring part 125 also includes the heating elements 123 and 124 as described in the first embodiment. Over the wiring part 125, the detection electrodes 131 and 132 constructing the humidity sensor 130 are formed via an interlayer insulating film 116 (for example, a silicon oxide film). Although not shown in FIG. 13, the reference electrodes 134 and 135 are also formed in the same plane as the detection electrodes 131 and 132. Over the detection electrodes 131 and 132, the moisture sensitive film 133 is formed via a protection film 117 (for example, a silicon nitride film).

In the semiconductor substrate 110, the cavity 111 for flow and the cavity 118 for dehumidification are formed in correspondence with the flow sensor 120 and the humidity sensor 130, respectively. The cavity 118 for dehumidification is formed so as to include the moisture sensitive film 133 in the plane direction of the semiconductor substrate 100. The cavity 111 for flow and the cavity 118 for dehumidification are formed using the insulating film 115 as the bottom. The thin portion 112 and a thin portion 119 as an insulating film are formed over the cavity 111 for flow and the cavity 118 for dehumidification, respectively. The wiring part 125 made of, for example, polysilicon doped with an impurity is formed so that, as shown in FIG. 14, the heating element 121 having higher temperature is narrower than the dehumidification heater 136.

As described above, in the semiconductor device 100 of the fifth embodiment, the moisture sensitive film 133 can be recovered by evaporating the moisture captured in the moisture sensitive film 133 due to deterioration in the moisture sensitive film 133 by the dehumidification heater 136.

Since the humidifying heater 136 and the heating elements 121 and 122 are constructed as the single wiring part 125, the configuration can be simplified and the structure can be downsized. The manufacturing process can be also simplified.

When current is passed to the wiring part 125, both of the heating elements 121 and 122 and the dehumidification heater 136 generate heat. Therefore, for example, as described in the first embodiment, when the humidity sensor 130 is provided on the upstream side of the flow sensor 120, to recover the moisture sensitive film 133 by turning on the dehumidification heater 136, since the influence of the heat conduction from the dehumidification heater 136 to the flow sensor 120 via the fluid is considerably exerted, it is preferable not to use, for flow rate detection, a signal output from the flow sensor 120 at the timing when the dehumidification heater 136 is on. As described in the third embodiment, when the humidity sensor 130 is provided in parallel with the flow sensor 120 and the flow of the fluid, processes similar to the above may be performed. Since the influence of heat conduction from the dehumidification heater 136 to the flow sensor 120 via the fluid is less than the above, the signal output from the flow sensor 120 at the timing when the dehumidification heater 136 is turned on can be also used for flow detection.

Figure 15:
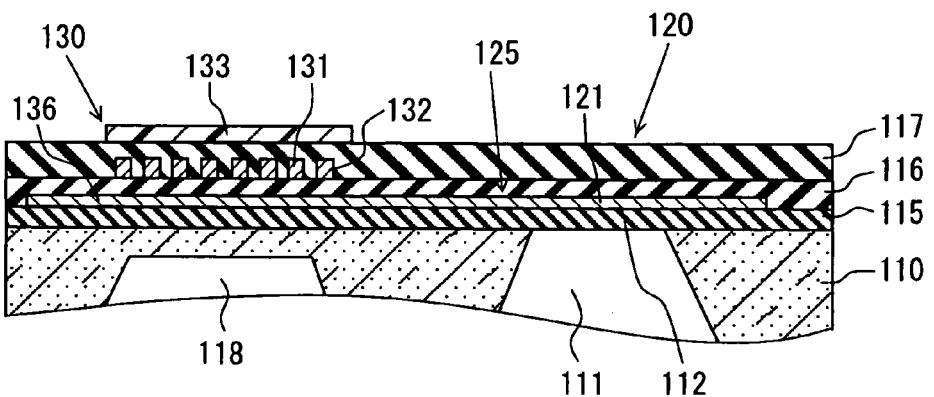
FIG. 15 is a cross section showing a modification of the fifth embodiment.

In the fifth embodiment, by varying the width of the wiring part 125, the temperature on the heating elements 121 and 122 and that of the dehumidification heater 136 are made different from each other. Alternatively, for example, as shown in FIG. 15, the depth of the cavity 111 for flow and that of the cavity 118 for dehumidification as the low heat conduction areas may be different from each other (in FIG. 15, the cavity 118 for dehumidification corresponding to the dehumidification heater 136 of lower temperature is shallower than the cavity 111 for flow). With such a configuration, the amount of heat conduction to the semiconductor substrate 110 side in the heating elements 121 and 122 and that in the dehumidification heater 136 are made different from each other and, moreover, the temperature of each of the flow sensor 120 and the humidity sensor 130 can be made proper. FIG. 15 is a cross section showing a modification.

Figure 16:
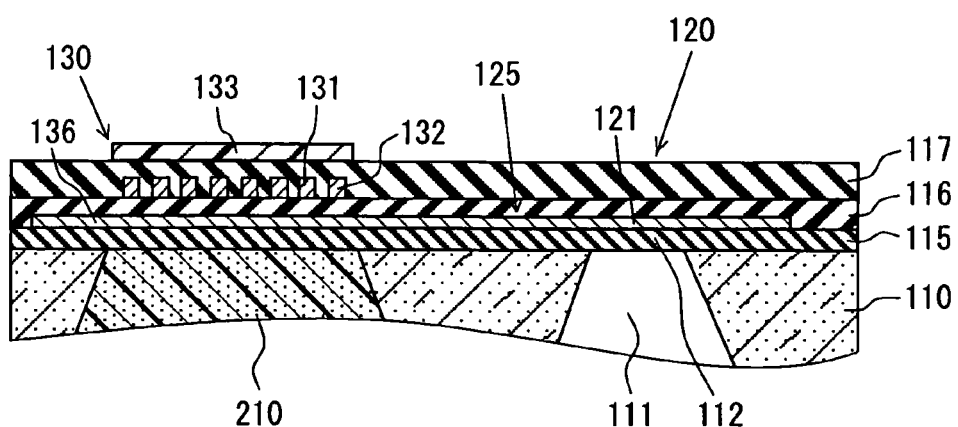
FIG. 16 is a cross section showing a second modification of the fifth embodiment.

In the fifth embodiment, the cavity 111 for flow is formed as the low thermal conduction area in an area just below the heating elements 121 and 122, and the cavity 118 for dehumidification is formed in the area just below the humidity sensor 130 in the semiconductor substrate 110. However, the low thermal conduction area is not limited to the cavity. It is sufficient for the low thermal conduction area to have thermal conductivity lower than that of the semiconductor substrate 110. For example, the low thermal conduction area may be formed by a porous member (for example, porous silicon or porous insulating film). For example, one of the low thermal conduction area corresponding to the heating elements 121 and 122 and the low thermal conduction area corresponding to the humidity sensor 130 may be formed as a cavity. In the other area, porous silicon may be disposed. As an example, in FIG. 16, the low thermal conduction area corresponding to the heating elements 121 and 122 is formed as the cavity 111 for flow, and the low thermal conduction area corresponding to the humidity sensor 130 is formed as a porous silicon part 210 made of porous silicon. Such a porous silicon part 210 can be formed by, for example, local electrochemical melting reaction. With such a configuration, by making the thermal conductivity vary between the cavity and the porous silicon, the amount of heat conduction to the semiconductor substrate 110 side in the heating elements 121 and 122 and that in the dehumidification heater 136 can be made different from each other. FIG. 16 is a cross section showing a modification.

The configurations in the foregoing embodiments and modifications can be combined.

Although the preferred embodiments of the present disclosure have been described above, the disclosure is not limited to the embodiments but can be variously modified without departing from the gist of the disclosure.

In the embodiment, the silicon substrate is used as an example of the semiconductor substrate 110. However, the semiconductor substrate 110 is not limited to the silicon substrate.

In the embodiments, the flow sensor 120 has the heating elements 121 and 122 and also the temperature sensing elements 123 and 124. However, to detect the flow of the fluid, it is sufficient for the flow sensor 120 to have at least the heating elements 121 and 122. Consequently, a configuration including no temperature sensing elements 123 and 124 may be also employed.

In the embodiments, the humidity sensor 130 has the reference electrodes 134 and 135. However, a configuration including no reference electrodes 134 and 135 may be also employed.

In the embodiment, the circuit part 140 is formed together with the flow sensor 120 and the humidity sensor 130 over the same semiconductor substrate 110. That is, the circuit part 140 is formed together with the flow sensor 120 and the humidity sensor 130 on one chip. It is also possible to form the circuit part 140 on a different substrate. In this case, the substrate on which the circuit part 140 is formed is completely covered with the encapsulation resin 190. The function of the circuit part 140 may be provided (for example, for an external ECU) separately from the semiconductor device 100.

In the embodiments, in a state where the semiconductor substrate 110 is fixed to the supporting member 180, a part of the semiconductor substrate 110 is covered with the encapsulation resin 190. However, a configuration having no supporting member 180 may be also employed. When the supporting member 180 is a part of the lead frame as described in the embodiment, positional deviation of the semiconductor substrate 110 can be suppressed at the time of covering with the encapsulation resin 190 (for example, at the time of transfer molding). The shape of the supporting member 180 is not limited to that described in the embodiment.

The above disclosure has the following aspects.

According to a first aspect of the present disclosure, a semiconductor device includes: a semiconductor substrate; a flow sensor having a first heater for detecting a flow rate of fluid; and a humidity sensor for detecting a humidity of the fluid. The flow sensor and the humidity sensor are disposed on the semiconductor substrate. The flow sensor is disposed around the humidity sensor. The humidity sensor is disposed on an upstream side of the first heater.

Since the above device includes the humidity sensor, moisture in the fluid is compensated so that detection accuracy of the flow rate is improved. Further, the humidity sensor is disposed near the flow sensor, the humidity near the flow sensor is detected by the humidity sensor so that the detection accuracy of the flow rate is much improved. Furthermore, since the humidity sensor and the flow sensor are disposed on the same substrate, the dimensions of the device are minimized. Further, the humidity sensor is not substantially affected by heat generated by a heater in the flow sensor humidity sensor. Thus, the detection accuracy of the flow rate is improved.

Alternatively, the humidity sensor may be adjacent to the humidity sensor along with a flowing direction of the fluid. Alternatively, the semiconductor device may further include: a pad disposed on the substrate; a resin sealing member; and a polymer film for increasing adhesiveness between the semiconductor substrate and the resin sealing member. The humidity sensor and the flow sensor output detection signals through the pad. The pad is coupled with an external terminal at a connection portion. The resin sealing member covers a part of the substrate, the part which includes the connection portion and does not include the humidity sensor and the flow sensor. The polymer film is partially disposed between the part of the substrate and the resin sealing member. The humidity sensor includes a pair of electrodes and a humidity sensitive film. The pair of electrodes is made of conductive material, and disposed on the substrate. The humidity sensitive film is disposed on the substrate and disposed between the pair of electrodes. The humidity sensitive film has a relative permittivity or an impedance, which is changeable in accordance with humidity change, and the humidity sensitive film and the polymer film are made of a same material. Further, the humidity sensitive film and the polymer film may be partially integrated. Alternatively, the humidity sensitive film and the polymer film may be separated. Further, the polymer film may be completely covered with the resin sealing member.

Alternatively, the humidity sensitive film may be made of poly-imide. Further, the poly-imide may include a plurality of molecular chains for providing a network structure, and both ends of each chain are connected.

Alternatively, the semiconductor device may further include: a second heater for heating the humidity sensor. The second heater is disposed on the substrate. The first and second heaters are provided by a same wire. The first and second heaters are integrated. Further, the substrate may further include a first low heat conduction portion and a second low heat conduction portion. The first low heat conduction portion is disposed under the first heater. The second low heat conduction portion is disposed under the humidity sensor. Each of the first and second low heat conduction portions has a heat conduction lower than a heat conduction of other parts of the semiconductor substrate. The first low heat conduction portion has a first depth in a thickness direction of the semiconductor substrate. The second low heat conduction portion has a second depth in the thickness direction of the semiconductor substrate. The first depth is different from the second depth. Furthermore, each of the first and second low heat conduction portions may be provided by a concavity of the substrate. Alternatively, each of the first and second low heat conduction portions may be provided by a porous silicon part of the substrate.

Alternatively, the substrate may further include a first low heat conduction portion and a second low heat conduction portion. The first low heat conduction portion is disposed under the first heater. The second low heat conduction portion is disposed under the humidity sensor. Each of the first and second low heat conduction portions has a heat conduction lower than a heat conduction of other parts of the semiconductor substrate. One of the first and second low heat conduction portions is provided by a concavity of the substrate, and the other one of the first and second low heat conduction portions is provided by a porous silicon part of the substrate.

Alternatively, the first heater may have a first width, which is different from a second width of the second heater.

Alternatively, the flow sensor and the humidity sensor may be disposed on a same side of the semiconductor substrate. The substrate further includes a groove, which is disposed between the first heater and the humidity sensor, and the groove has a predetermined depth in a thickness direction of the substrate.

According to a second aspect of the present disclosure, a semiconductor device includes: a semiconductor substrate; a flow sensor for detecting a flow rate of fluid; a humidity sensor for detecting a humidity of the fluid; a resin mold for molding a part of the semiconductor substrate; and a lead terminal, a part of which is molded in the resin mold. The flow sensor and the humidity sensor are disposed on another part of the semiconductor substrate so that the flow sensor and the humidity sensor are not covered with the resin mold. The humidity sensor is disposed on an upstream side of the first heater. The semiconductor substrate includes a concavity and a pad. The concavity is disposed opposite to the humidity sensor and the flow sensor. The pad is disposed on the substrate. The humidity sensor and the flow sensor are coupled with the pad so that the humidity sensor and the flow sensor output detection signals through the pad. The pad is coupled with the lead terminal with a wire. The resin mold molds a connection portion between the pad and the wire and the wire.

Since the above device includes the humidity sensor, moisture in the fluid is compensated so that detection accuracy of the flow rate is improved. Further, the humidity sensor is disposed near the flow sensor, the humidity near the flow sensor is detected by the humidity sensor so that the detection accuracy of the flow rate is much improved. Furthermore, since the humidity sensor and the flow sensor are disposed on the same substrate, the dimensions of the device are minimized. Further, the humidity sensor is not substantially affected by heat generated by a heater in the flow sensor humidity sensor. Thus, the detection accuracy of the flow rate is improved.

Alternatively, the device may further include: a polymer film for increasing adhesiveness between the semiconductor substrate and the resin mold. The polymer film is partially disposed between the part of the substrate and the resin mold. The humidity sensor includes a pair of electrodes and a humidity sensitive film. The pair of electrodes is made of conductive material, and disposed on the substrate. The humidity sensitive film is disposed on the substrate and disposed between the pair of electrodes. The humidity sensitive film has a relative permittivity or an impedance, which is changeable in accordance with humidity change, and the humidity sensitive film and the polymer film are made of a same material.

While the invention has been described with reference to preferred embodiments thereof, it is to be understood that the invention is not limited to the preferred embodiments and constructions. The invention is intended to cover various modification and equivalent arrangements. In addition, while the various combinations and configurations, which are preferred, other combinations and configurations, including more, less or only a single element, are also within the spirit and scope of the invention.

What is claimed is:

1. A semiconductor device comprising:
   a semiconductor substrate;
   a flow sensor having a first heater for detecting a flow rate of fluid;
   a humidity sensor for detecting a humidity of the fluid;
   a pad disposed on the substrate;
   a resin sealing member; and
   a polymer film for increasing adhesiveness between the semiconductor substrate and the resin sealing member, wherein
   the flow sensor and the humidity sensor are disposed on the semiconductor substrate,
   the flow sensor is disposed around the humidity sensor,
   the humidity sensor is disposed on an upstream side of the first heater,
   the humidity sensor and the flow sensor output detection signals through the pad,
   the pad is coupled with an external terminal at a connection portion,
   the resin sealing member covers a part of the substrate that includes the connection portion and does not include the humidity sensor and the flow sensor,
   the polymer film is partially disposed between the part of the substrate and the resin sealing member,
   the humidity sensor includes a pair of electrodes and a humidity sensitive film,
   the pair of electrodes is made of conductive material, and disposed on the substrate,
   the humidity sensitive film is disposed on the substrate and disposed between the pair of electrodes,
   the humidity sensitive film has a relative permittivity or an impedance, which is changeable in accordance with humidity change, and
   the humidity sensitive film and the polymer film are made of a same material.

2. The semiconductor device according to claim 1, wherein the humidity sensor is adjacent to the flow sensor along a flowing direction of the fluid.

3. The semiconductor device according to claim 1, wherein the humidity sensitive film and the polymer film are partially integrated.

4. The semiconductor device according to claim 1, wherein the humidity sensitive film and the polymer film are separated.

5. The semiconductor device according to claim 4, wherein the polymer film is completely covered with the resin sealing member.

6. The semiconductor device according to claim 1, wherein the humidity sensitive film is made of poly-imide.

7. The semiconductor device according to claim 6, wherein the poly-imide includes a plurality of molecular chains for providing a network structure, and both ends of each chain are connected.

8. The semiconductor device according to claim 1, further comprising:
   a second heater for heating the humidity sensor, wherein the second heater is disposed on the substrate,
   the first and second heaters are provided by a same wire, and
   the first and second heaters are integrated.

9. The semiconductor device according to claim 8, wherein
   the substrate further includes a first low heat conduction portion and a second low heat conduction portion,
   the first low heat conduction portion is disposed under the first heater,
   the second low heat conduction portion is disposed under the humidity sensor,
   each of the first and second low heat conduction portions has a heat conduction lower than a heat conduction of other parts of the semiconductor substrate,
   one of the first and second low heat conduction portions is provided by a concavity of the substrate, and
   the other one of the first and second low heat conduction portions is provided by a porous silicon part of the substrate.

10. The semiconductor device according to claim 8, wherein the first heater has a first width, which is different from a second width of the second heater.

11. The semiconductor device according to claim 8, wherein
   the substrate further includes a first low heat conduction portion and a second low heat conduction portion,
   the first low heat conduction portion is disposed under the first heater,
   the second low heat conduction portion is disposed under the humidity sensor,
   each of the first and second low heat conduction portions has a heat conduction lower than a heat conduction of other parts of the semiconductor substrate,
   the first low heat conduction portion has a first depth in a thickness direction of the semiconductor substrate,
   the second low heat conduction portion has a second depth in the thickness direction of the semiconductor substrate, and
   the first depth is different from the second depth.

12. The semiconductor device according to claim 11, wherein each of the first and second low heat conduction portions is provided by a concavity of the substrate.

13. The semiconductor device according to claim 11, wherein each of the first and second low heat conduction portions is provided by a porous silicon part of the substrate.

14. The semiconductor device according to claim 1, wherein the flow sensor and the humidity sensor are disposed on a same side of the semiconductor substrate, the substrate further includes a groove, which is disposed between the first heater and the humidity sensor, and the groove has a predetermined depth in a thickness direction of the substrate.

* * * * *